(12) United States Patent
Bornmann

(10) Patent No.: US 11,738,335 B2
(45) Date of Patent: Aug. 29, 2023

(54) ADAPTER FOR RECEIVING A CAPILLARY

(71) Applicant: ALS Automated Lab Solutions GmbH, Jena (DE)

(72) Inventor: Gerd Bornmann, Weimar (DE)

(73) Assignee: ALS Automated Lab Solutions GmbH, Jena (DE)

( * ) Notice: Subject to any disclaimer, the term of this patent is extended or adjusted under 35 U.S.C. 154(b) by 85 days.

(21) Appl. No.: 16/781,780

(22) Filed: Feb. 4, 2020

(65) Prior Publication Data

US 2020/0171480 A1 Jun. 4, 2020

Related U.S. Application Data

(63) Continuation of application No. PCT/EP2018/071210, filed on Aug. 4, 2018.

(30) Foreign Application Priority Data

Aug. 4, 2017 (DE) .............. 10 2017 117 789.2

(51) Int. Cl.
   *B01L 3/02* (2006.01)
(52) U.S. Cl.
   CPC .......... *B01L 3/022* (2013.01); *B01L 3/0275* (2013.01); *B01L 2300/041* (2013.01); *B01L 2300/0838* (2013.01); *B01L 2300/123* (2013.01)
(58) Field of Classification Search
   None
   See application file for complete search history.

(56) References Cited

U.S. PATENT DOCUMENTS

| | | | |
|---|---|---|---|
| 7,335,337 B1 * | 2/2008 | Smith | B01L 3/0275 422/513 |
| 9,566,579 B1 * | 2/2017 | Kozlenko | B01L 3/0279 |
| 9,751,085 B2 | 9/2017 | Pa | |
| 9,822,331 B2 | 11/2017 | Backhaus et al. | |
| 10,471,421 B2 | 11/2019 | Cremien et al. | |
| 10,900,009 B2 | 1/2021 | Backhaus et al. | |

(Continued)

FOREIGN PATENT DOCUMENTS

DE   32 39 820 A1   5/1984
EP   2 674 481 A1   12/2013
(Continued)

OTHER PUBLICATIONS

International Search Report dated Nov. 14, 2018 of international application PCT/EP2018/071210 on which this application is based.
(Continued)

*Primary Examiner* — Brian R Gordon
(74) *Attorney, Agent, or Firm* — Walter Ottesen, P.A.

(57) ABSTRACT

An adapter assembly for receiving a capillary includes a passage, into which the capillary is or can be received. The adapter assembly has an adapter cone which is configured for being received in or on a correspondingly configured counter cone. The adapter cone, at least over a section for bringing the adapter cone into contact with the counter cone, includes an elastic material that is more elastic than the material of the counter cone. The invention further relates to a counterpart for connecting to the adapter, to an apparatus and to a method for automatically exchanging capillaries.

9 Claims, 12 Drawing Sheets

(56) References Cited

U.S. PATENT DOCUMENTS

| | | |
|---|---|---|
| 2004/0226389 A1 | 11/2004 | Thom et al. |
| 2008/0095665 A1 | 4/2008 | Smith |
| 2012/0284991 A1* | 11/2012 | Kusz ............... A61M 39/12 137/315.01 |
| 2013/0330248 A1 | 12/2013 | Shioyama et al. |
| 2014/0338430 A1 | 11/2014 | Theodorsen |
| 2015/0355212 A1 | 12/2015 | Ziechner |
| 2016/0332157 A1* | 11/2016 | Uda ............... B01L 3/563 |
| 2017/0189899 A1 | 7/2017 | Gupta |
| 2018/0030397 A1 | 2/2018 | Backhaus et al. |
| 2018/0117584 A1* | 5/2018 | Cote ............... B01L 3/0217 |

FOREIGN PATENT DOCUMENTS

| | | |
|---|---|---|
| EP | 3 159 399 A1 | 4/2017 |
| JP | 2004-337852 A | 12/2004 |
| WO | 01/73338 A1 | 10/2001 |
| WO | 2008/034868 A2 | 3/2008 |
| WO | 2009/040274 A2 | 4/2009 |
| WO | 2013/012588 A1 | 1/2013 |
| WO | 2014/007820 A1 | 1/2014 |
| WO | 2015/007853 A1 | 1/2015 |
| WO | 2017/040794 A1 | 3/2017 |
| WO | 2017/116960 A2 | 7/2017 |

OTHER PUBLICATIONS

Translation of the office action of the Japanese Patent Office dated Jun. 13, 2022 in corresponding Japanese patent application 2020-505867.

* cited by examiner

ADAPTER FOR RECEIVING A CAPILLARY

CROSS REFERENCE TO RELATED APPLICATIONS

This application is a continuation application of international patent application PCT/EP2018/071210, filed Aug. 4, 2018, designating the United States and claiming priority from German application 10 2017 117 789.2, filed Aug. 4, 2017, and the entire content of both applications is incorporated herein by reference.

FIELD OF THE INVENTION

The invention relates to an adapter for receiving a capillary. The adapter includes a passage in which the capillary is received or can be received. The adapter includes an adapter cone which is configured to be received in or on a correspondingly formed counter cone. The invention further relates to an adapter comprising a capillary, to an assembly and to an apparatus including the adapter as well as a method for automatically exchanging capillaries.

BACKGROUND OF THE INVENTION

In the field of cell biology and in the medical field, micromanipulators are used to remove or add individual cells, cell components or small amounts of media. In this process, capillaries, which are usually made of glass, are used as tools. Such a capillary is replaced manually, and this is usually laborious and prone to errors.

In many scientific and clinical studies, there is currently a trend towards studying individual cells rather than cell colonies. At the same time, the requirements for the quality of the individual work steps are increasing, and therefore the provision, manipulation and handling of individual cells are limiting factors in these processes.

The miniaturization of the test batches means that very small volumes need to be handled, in particular pipetted. The capillaries that are often used for this purpose have opening sizes in the low to medium micrometer range and, due to the very small volumes to be conveyed in the nanoliter range down to the lowest microliter range, have particularly high requirements on the leak-tightness of their connection to the connected pump system. In order to connect glass capillaries to a pump system, these are currently clamped by means of sealing rings, fittings or ferrules or are provided with adapters for being screwed in. If the capillaries are to be replaced automatically, these fastening methods are not suitable.

Due to the rapidly increasing use of this technology in the clinical and pharmacological environment, it is becoming increasingly important to work in a completely sterile manner and to prevent the risk of contamination and cross-contamination. For this purpose, the tools used need to be replaced with sterile tools after each cell harvest and after changing the patient sample. In the cell handling area, the capillaries used are replaced with sterile capillaries.

While the detection and separation of a cell only takes seconds, manually replacing the capillary takes several minutes. The replacement of the capillary therefore represents a bottleneck in increasing the degree of automation and increasing the throughput.

WO 2008/034868 discloses a device which has a tool head comprising a receptacle which is formed from an inner cone and/or an outer cone, and holds a removal tool in the form of a cannula, which has an inner cone and/or outer cone which fits to the receptacle. The conical receptacle results in self-centering of the capillaries, which can be positioned with high precision, by the tool. The high stability of the conical receptacle enables even force distribution and withstands relatively high lateral forces without any loss of position accuracy. By using a thickened portion below the conical receptacle, the replaceable capillary can be removed from the tool again by means of a stripping device.

SUMMARY OF THE INVENTION

An object of the invention is to provide a configuration of a replaceable capillary comprising an adapter assembly which is improved compared with the prior art and to achieve a high level of leak-tightness and at the same time high position accuracy.

An adapter assembly of the invention is for accommodating a capillary. The adapter assembly includes: an adapter cone having a passage for receiving the capillary therein; the adapter cone having a first conical surface; a counter cone having a second conical surface formed thereon corresponding in conjugation to the first conical surface so as to permit the adapter cone to be received in or on the second conical surface causing the first and second conical surfaces to conjointly define a conical interface; the counter cone being made of a first material having a first elasticity; the adapter cone having at least one section thereof configured to bring the adapter cone into contact with the counter cone at the interface; and, the at least one section being made of a second material having a second elasticity greater than the first elasticity.

The adapter is configured to receive a capillary and comprises a passage in which the capillary is received or can be received. In addition, the adapter comprises an adapter cone which is configured to be received in or on a correspondingly formed counter cone.

According to the invention, the adapter cone consists of a resilient material at least over a portion which is provided and configured to bring the adapter cone into contact with the counter cone. The resilient material is more resilient than the material of the counter cone.

Within the meaning of this description, the resilient material has a modulus of elasticity E=<10 GPa, preferably less than or equal to 5 GPa, in particular less than 3 GPa. Such resilient materials are, for example, plastics materials such as polypropylene (PP; E=1.3-1.8 GPa), polyethylene (PE; 1 GPa), polytetrafluoroethylene (PTFE; 0.4 GPa), polyvinyl chloride (PVC; 3 GPa), polyethylene terephthalate (PET; 3 GPa), polyether ether ketone (PEEK; 3.6 GPa), rubber (up to 0.05 GPa) or hard rubber (5 GPa).

The adapter cone can be configured either as an inner cone or an outer cone. The counter cone, which is formed on a counterpart that fits to the adapter, is correspondingly compatible as an inner or outer counter cone.

The key concept of the invention is for it to be possible to connect the adapter safely and securely to a correspondingly shaped and dimensioned counter cone, such that high lateral forces can be absorbed and at the same time reliable sealing is achieved, in particular of a capillary located in the passage of the adapter. The resilient material of the adapter cone ensures that a high level of leak-tightness is achieved despite manufacturing tolerances that occur.

The invention relates to the configuration and implementation of a mechanical interface for picking up and releasing capillaries in an automatable manner for the purpose of providing a reliable, tight and low-dead-volume connection to a pump system. In addition, the proposed invention reproduces the position of the capillary very precisely after being replaced, which is very important for the positioning of the capillary tip in relation to small particles to be transported (for example, cells having a size of approx. 10 µm). The invention is intended for use in the fields of biology, pharmacology, biochemistry and medicine, in which capillaries are used for the serial uptake and passage of individual small particles, biological samples, cells or small amounts of liquid in the nanoliter range.

The invention solves the technical problem of coordinating the cone geometry of the adapter with the counter-cone geometry and at the same time ensuring leak-tightness and mechanical resilience despite the configuration as a replaceable technical element. It is advantageously achieved that the upper end of the adapter cone, for example, also ends at the upper end of the counter cone, without losing the clamping effect of the cones as a result of manufacturing tolerances. This is achieved by means of the resilient material, the elasticity of which allows manufacturing tolerances to be compensated for. In addition, the probability of the occurrence of dead volumes is reduced.

In this case, the entire adapter cone can consist of a resilient material that is significantly more resilient than the material of the counter cone. Using such an embodiment according to the invention, manufacturing tolerances are compensated for and high leak-tightness is ensured. However, the positional accuracy can be reduced, which means that it is difficult to pick up small objects, for example, cells.

It is also possible that only the material which is intended to be brought into direct contact with the counter cone is more resilient than the material of the counter cone. Under the resilient material, the adapter cone can consist of a considerably more rigid material.

The resilient material can be bonded to and/or inserted into the adapter cone. The adapter can also be produced, for example, by means of two-component injection molding.

In an advantageous further embodiment of the adapter according to the invention, the portion is formed in the region of the free end of the adapter cone. The free end is the end of the adapter cone with which the adapter is first plugged into the counter cone. In this embodiment, the material of the adapter cone lying against the counter cone is merely less resilient or not more resilient than the material of the counter cone. The portion having the resilient material is located at the free end of the adapter cone, such that a dead volume region that may arise is minimized after the adapter has been plugged into the counter cone.

Additionally or alternatively, a seal can be provided at the free end of the adapter cone, the effect of which results in an additional seal on the end face. This seal may also be part of the portion made of the resilient material.

The adapter cone can furthermore have one, two or more sealing elements which are configured, for example, in the form of sealing rings, sealing lips and/or O-rings. These sealing elements may, for example, be pushed onto or molded onto the adapter cone and advantageously extend over the relevant circumference of the adapter cone.

A capillary may be arranged in the passage of the adapter. In order to avoid the end-face seal narrowing or even closing the passage in the event of a deformation when the adapter cone is connected to the counter cone, the seal can easily be inserted into the end face of the adapter cone. The capillary protruding prevents an undesirable reduction in the free cross section of the passage or the capillary due to the deformed seal.

In order to make it possible to easily remove the adapter from the counter cone, the adapter has a change in cross section in a region facing away from the adapter cone. The change in cross section is configured to engage a gripping tool, ejector or stripper and is produced, for example, as a groove, joint, step or convex portion.

This change in cross section can also be used to store the adapter, preferably together with a capillary, in a storage container, for example a rack or other magazine, and to keep it available for automated removal, for example. The adapter can also be released into a storage container, for example in an automated manner. Therefore, the configuration of the geometry of the adapter adjoining the adapter cone makes it possible both to easily strip and to securely store the capillaries with their often-sensitive tips.

The counter cone is formed on a counterpart which is, for example, part of a device such as a pipetting unit, a micromanipulator, or a picker unit.

The counter cone consists of a material which has a modulus of elasticity of at least 20 GPa over the portion thereof that is in contact with the adapter cone or is to be brought into contact with the adapter cone. For example, the counter cone consists of V2A steel (180 GPa), brass (78-123 GPa) or ceramic (160-440 GPa).

As already described, the adapter, which can optionally hold a capillary, and the counter cone form an assembly that allows for high position accuracy and at the same time can absorb high lateral forces. The adapter is configured such that it is connected in a self-locking and self-centering manner to a corresponding counter cone due to the cone pitch and the material pairing. A capillary retained by the adapter maintains its relative position and orientation even when the adapter moves. The dimensions of the adapter cone and counter cone can advantageously be based on standard sizes and cone angles, as are known, for example, from cone tool holders (Morse holders, et cetera).

In an advantageous embodiment, a connection region of the counterpart is provided, the connection region being configured for releasably connecting the counterpart to a device. The counterpart can thus be replaced if, for example, differently sized adapters or differently sized adapters having capillaries are to be used.

In order to connect an adapter tightly to a capillary, this can be bonded to or overmolded on the adapter, for example. Alternatively or additionally, a seal can be present in the passage, the effect of which seals the capillary against the passage. The capillary may be made of different materials such as glass, metal, ceramic, plastics material or combinations thereof.

The adapter, in particular together with the counterpart, can be used in a method for automatically replacing capillaries. The method can also serve to pick up and release bodies such as cells, small cell clusters, small particles (for example, beads) and small volumes in the nanoliter range in a targeted manner. The method may comprise the following steps:

picking up the adapter comprising a capillary from a storage container, using the capillary for picking up and/or transporting the bodies and/or volumes, stripping or discarding the used adapter, for example by approaching a stationary stripper, or releasing the adapter in a targeted manner into an addressable parking or waiting position by means of a ejector, which can be integrated in the counterpart.

The method can also be carried out using a plurality of adapters comprising capillaries in parallel to increase the throughput.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
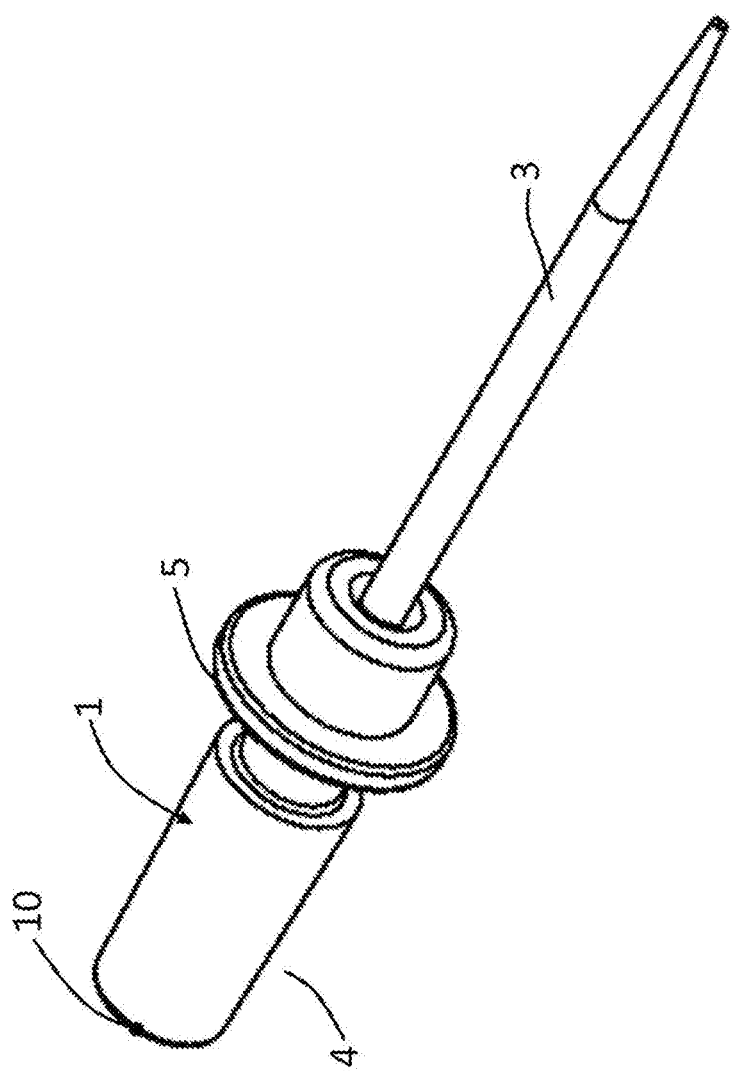
FIG. 1 is a schematic perspective view of a first embodiment of an adapter according to the invention comprising a capillary.

In the schematic of a first embodiment of an adapter 1 according to the invention in FIG. 1, a capillary 3 is inserted into a passage 2 (see FIGS. 4 to 7) in the adapter 1 and tightly connected thereto. The adapter 1 comprises an adapter cone 4 in the form of an outer cone. This consists of a resilient material 10 having a modulus of elasticity of =<10, preferably <5 GPa. In addition, the adapter 1 has a change 5 in cross section in the form of a rotationally symmetrical convex portion.

Figure 2:
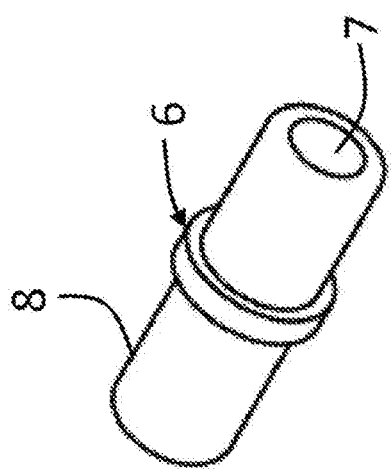
FIG. 2 is a schematic view of a first embodiment of a counterpart.

FIG. 2 schematically shows a counterpart 6, which has a counter cone 7 in the form of an inner cone and a connection region 8. The counter cone 7 is dimensioned in such a way that the adapter cone 4 can be inserted therein and the two cones 4 and 7 can be used to produce a force-locked/form-locked, releasable connection between the adapter 1 and the counterpart 6. The connection region 8 is configured as an outer cone and serves to connect the counterpart 6 to a device 13 (see FIG. 12).

In the embodiments described in this application, the adapter cone 4 is configured as an outer cone and the counter cone 7 is configured as an inner cone. In further possible configurations of the adapter 1 and the counterpart 6, the adapter cone 4 may be configured as an inner cone and the counter cone 7 may be configured as an outer cone.

Figure 3:
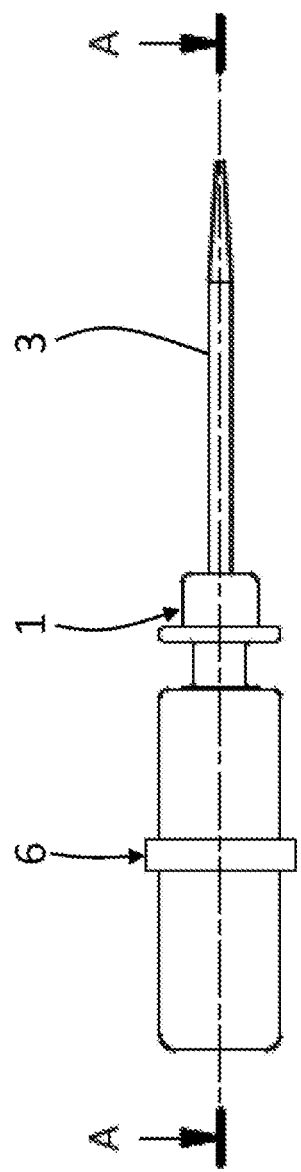
FIG. 3 is a schematic side view of a second embodiment of an adapter comprising the capillary inserted into the counterpart.

FIG. 3 is a side view of an adapter 1 comprising a capillary 3 that is inserted into the counterpart 6. The course of a sectional plane A-A is indicated longitudinally through the counterpart 6, adapter 1 and capillary 3.

Figure 4:
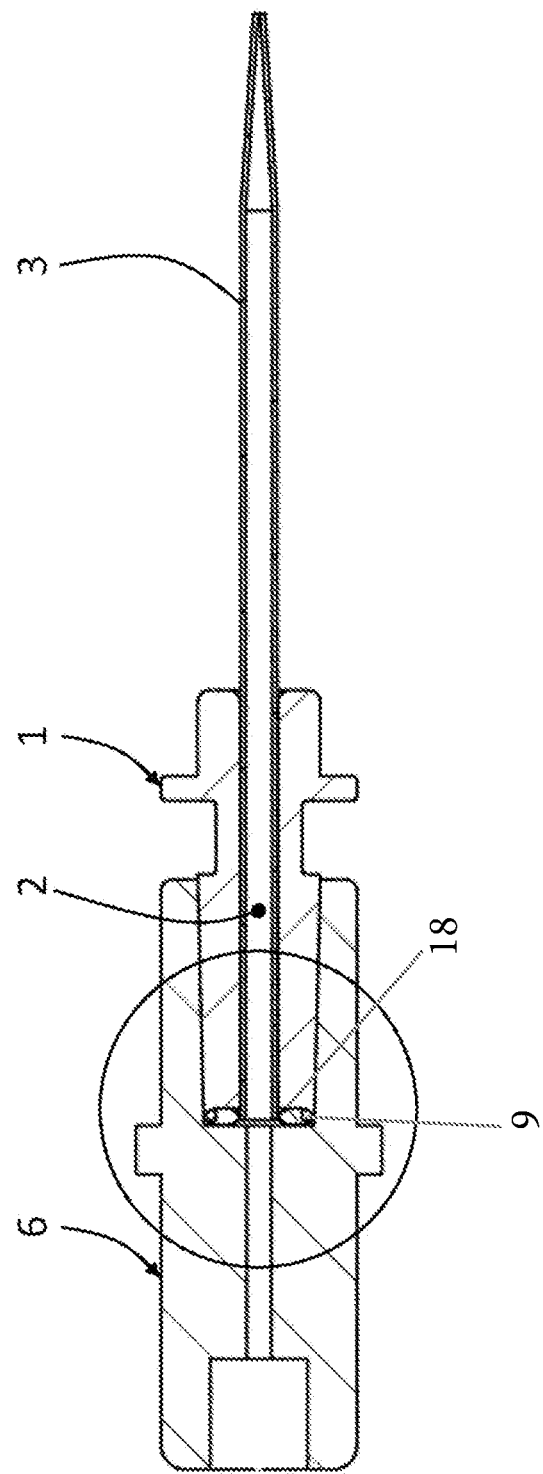
FIG. 4 is a schematic, partial sectional view of the inserted adapter, the capillary and the counterpart.

The section A-A shows the second embodiment of the adapter 1 according to the invention (FIG. 4). The adapter has a seal 9 on the end face 18 of a free end of the adapter cone 4. The adapter cone 4 is in contact with the counter cone 7 and extends as far as the rear end of the counter cone 7. The adapter cone 4 and the counter cone 7 each consist of a hard material such as a metal, a metal alloy, ceramic or a hard composite material.

Figure 5:
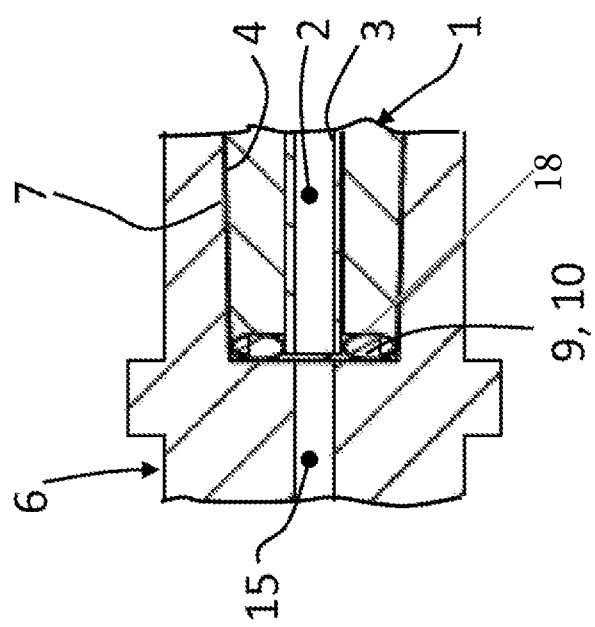
FIG. 5 is a schematic sectional view of an enlarged detail, circled in FIG. 4, of the inserted adapter, the capillary and the counterpart.

The seal 9 is configured as an O-ring made of a resilient material 10 and seals the inserted adapter 1 against the rear end of the counter cone 7 (FIG. 5). The seal 9 is part of the adapter 1. Alternatively, the seal 9 is not part of the adapter 1, but then the adapter cone 4 consists of the resilient material at least over a portion of its surface, in particular on the end face. In further embodiments, the seal 9 can also be combined with an adapter cone 4, which consists of the resilient material 10 at least over one portion or comprises this material over a portion.

An overpressure or negative pressure can be applied to the capillary 3 through a channel 15 that is present in the counterpart 6 and connects to the passage 2 and the capillary 3.

Figure 6:
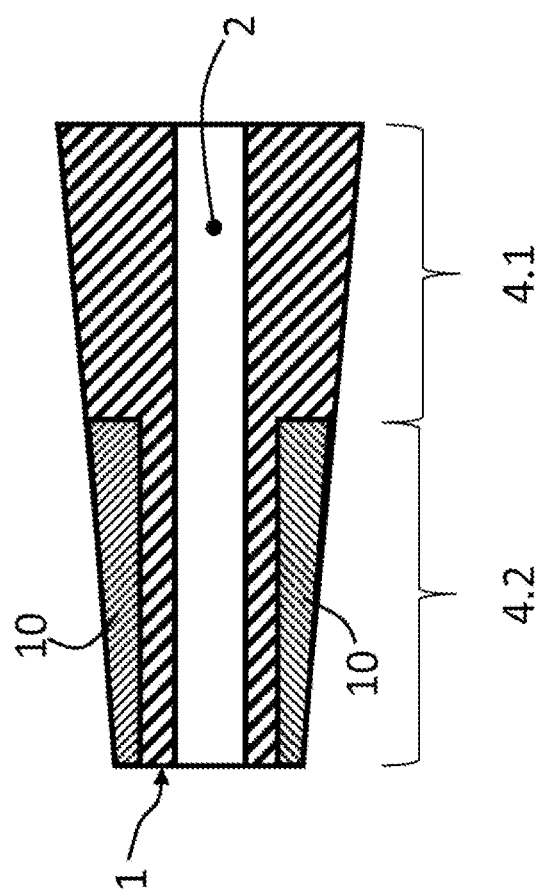
FIG. 6 is a schematic sectional view of an enlarged detail of a third embodiment of an adapter according to the invention.

In the third embodiment of the adapter 1 according to the invention shown in FIG. 6, its adapter cone 4 consists of a hard material over a first portion 4.1, while a resilient material 10 is inserted into the adapter cone 4 over a second portion 4.2. Alternatively, the resilient material 10 can also be applied to a region of the adapter 1 that has a smaller diameter than the adapter cone 4. In addition, a seal 9 (not shown; see FIG. 5) can be provided at the free end of the adapter cone 4.

Figure 7:
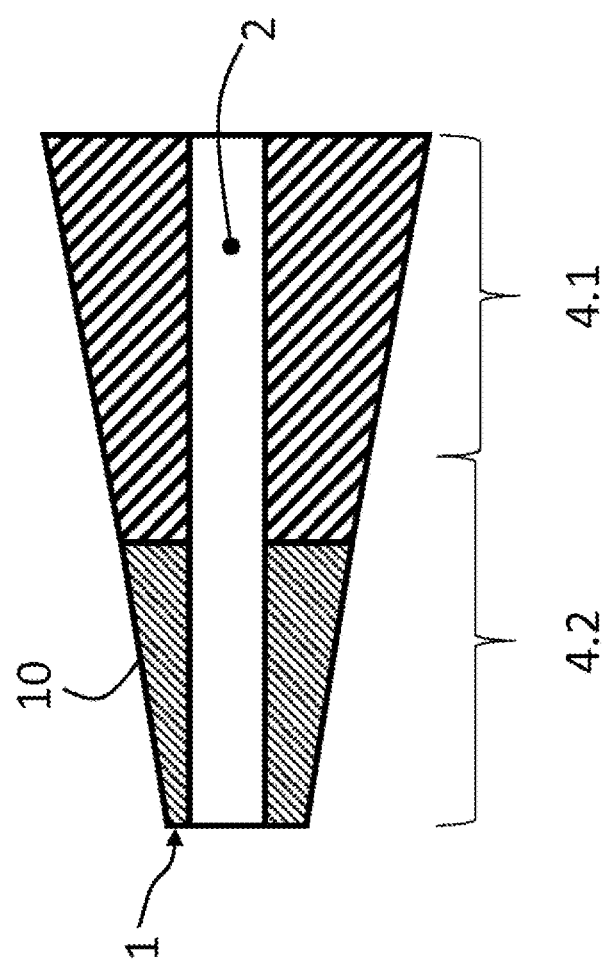
FIG. 7 is a schematic sectional view of an enlarged detail of a fourth embodiment of an adapter according to the invention.

The fourth embodiment of the adapter 1 according to the invention shown in FIG. 7 in turn has a first portion 4.1 of the adapter cone 4, which consists of a hard material. The second portion 4.2 is formed continuously from the resilient material 10.

Figure 8:
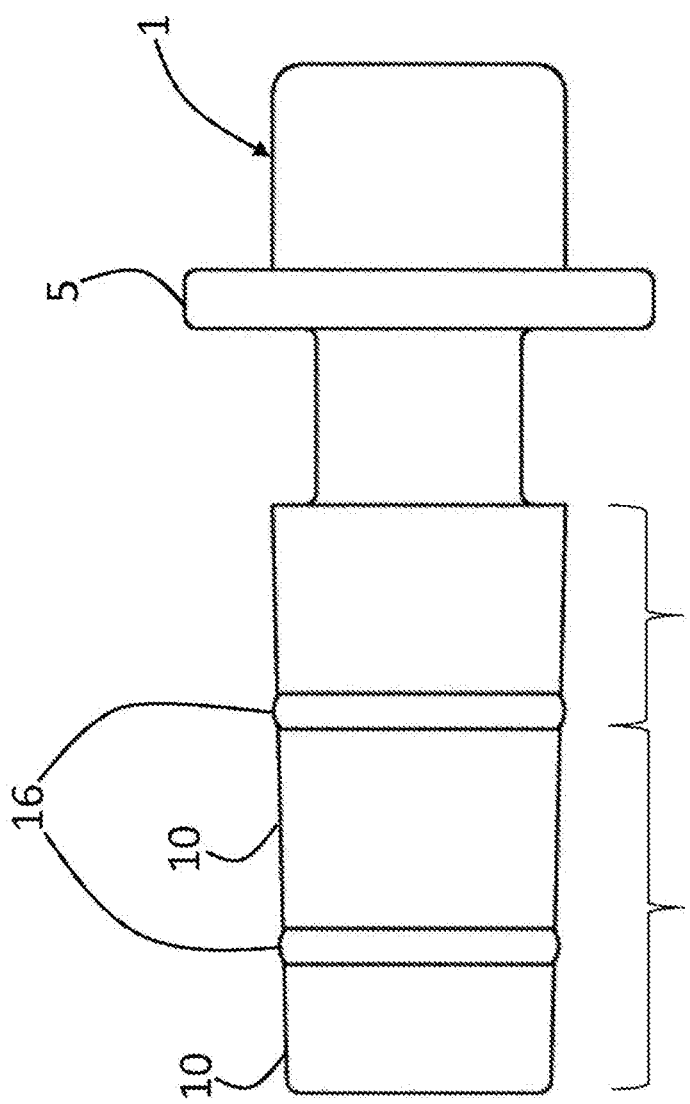
FIG. 8 is a schematic view of a fifth embodiment of an adapter according to the invention.

FIG. 8 shows a fifth embodiment of the adapter 1. In addition to the first and second portions 4.1 and 4.2, there are sealing elements 16 which are configured, for example, as O-rings and/or sealing lips. The sealing elements 16, of which only one or more than two can be present in other configurations, bring about additional retention of the adapter cone 4 on the counter cone 7 and increase the leak-tightness. Where necessary, alternatively or additionally, the flexibility of the adapter 1 in relation to the counter-cone 7 can be influenced, for example increased, by means of the sealing elements 16.

Figure 9:
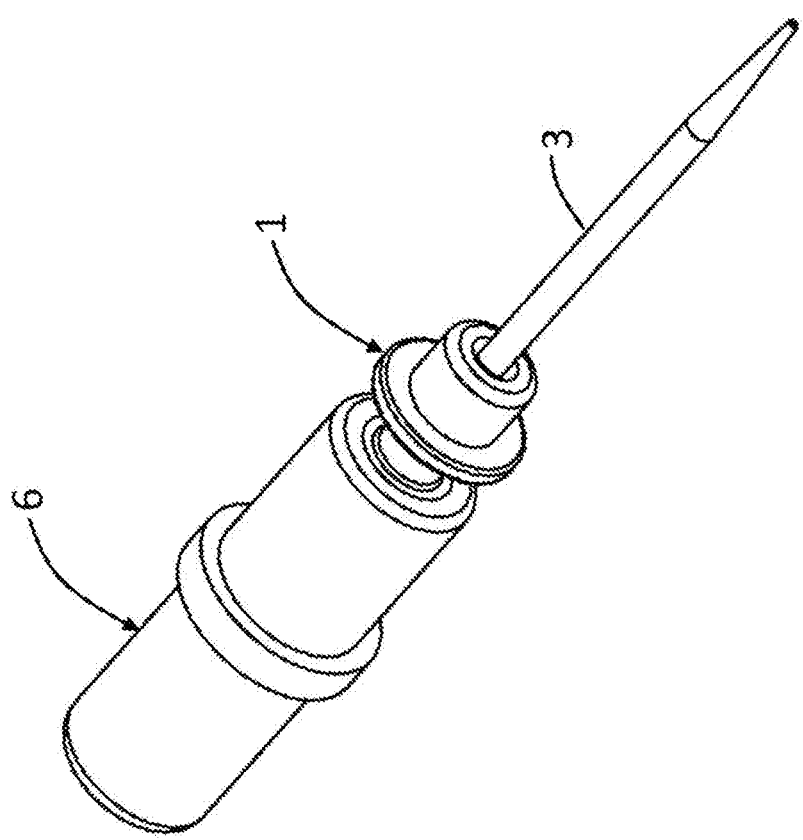
FIG. 9 is a schematic perspective view of the adapter comprising the capillary inserted into the counterpart.

FIG. 9 is a perspective view of the adapter 1 comprising the capillary 3 inserted into the counterpart 6.

Figure 10:
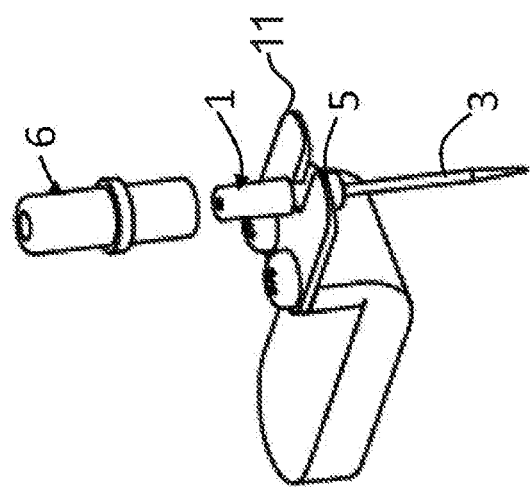
FIG. 10 is a schematic view of the adapter comprising the capillary, the counterpart and a stripper.

The change 5 in cross section serves for the engagement of a stripper 11 (see FIG. 10), the effect of which can pull the adapter 1 out of the counterpart 6.

Figure 11:
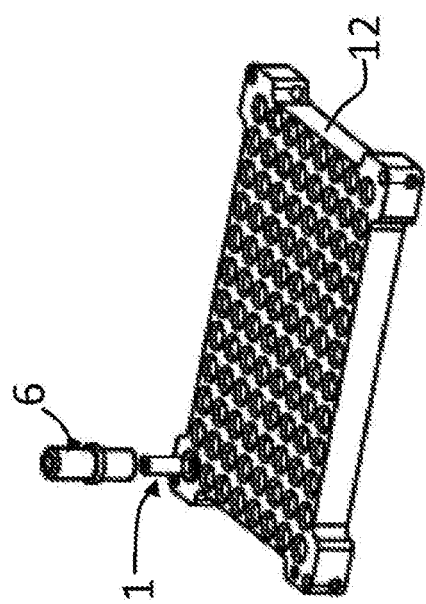
FIG. 11 is a schematic view of a storage container in the form of a rack and an adapter comprising a capillary and counterpart; and, FIG. 12 is a schematic view of a device comprising the counterpart, adapter and capillary.

The adapter 1 can be inserted into a slot in a storage container 12, for example a rack. FIG. 11 shows, in a simplified form, an adapter 1 which is stored in the storage container 12. If the counterpart 6 is plugged into the adapter cone 4, the adapter 1 can be removed from the storage container 12.

Figure 12:
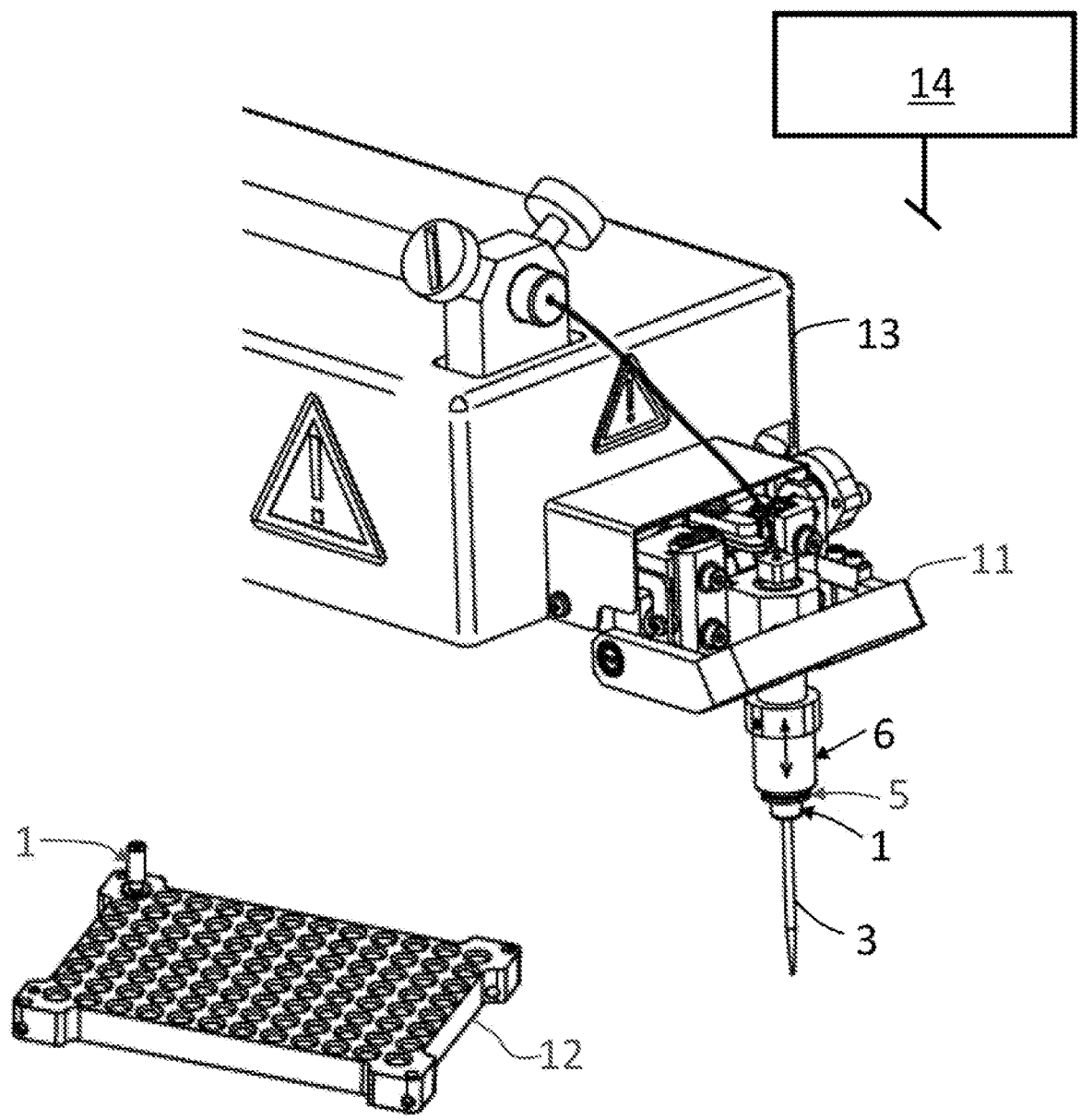

The adapter 1, the capillary 3 and the counterpart 6 can be used as parts of a device 13 which is, for example, a pipetting unit, a cell sorter or a micromanipulator (FIG. 12). The actuation of the device 13 and the generation of negative pressure or overpressure in the capillary 3 as well as movements for receiving the adapter 1, for discarding the adapter 1 and possibly for positioning the adapter are coordinated and triggered by means of a control unit 14.

It is understood that the foregoing description is that of the preferred embodiments of the invention and that various changes and modifications may be made thereto without departing from the spirit and scope of the invention as defined in the appended claims.

REFERENCE SIGNS 1 adapter
2 passage
3 capillary
4 adapter cone
4.1 first portion (of the adapter cone 4)
4.2 second portion (of the adapter cone 4)
5 change in cross section
6 counterpart
7 counter cone
8 connection region
9 seal
10 resilient material
11 stripper
12 storage container
13 device
14 control unit
15 channel
16 sealing elements

What is claimed is:

1. A system for automatically replacing capillaries, the system comprising:
an adapter assembly including:
a capillary having a forward end and a rearward end;
an adapter body having a passage in which said rearward end of said capillary is accommodated and said adapter body having a first conical surface facing away from said forward end of said capillary; and
a counterpiece having a connector end and having a second conical surface opposite to said connector end, said second conical surface corresponding in conjugation to said first conical surface; said adapter body is received in or on said second conical surface causing said first and second conical surfaces to be in mutual contact engagement and conjointly define a conical interface forming an interference fit;
said first conical surface being defined by a first material having a first elasticity;
said second conical surface being defined by a second material having a second elasticity different from said first elasticity to provide a sealing at said conical interface;
a holding device configured for holding said adapter body at a predetermined location;
a micromanipulator releasably holding said counterpiece on said connector end and configured for picking up said adapter body from said holding device;
a stripping device configured for receiving said adapter body from said micromanipulator and for disconnecting said adapter body from said counterpiece; and
a control unit configured to coordinate and trigger movements of the micromanipulator and/or the stripping device that cause the adapter body to be picked up from its predetermined holding location or to be discarded.

2. The system of claim 1, wherein said second material has a modulus of elasticity E=<10 GPa.

3. The system of claim 1, wherein the conical surface of said adapter body is configured either as a body having an interior defining a conical surface or as a body having an exterior defining an outer conical surface.

4. The system of claim 1, wherein said conical surface of said adapter body has an end face; and, said adapter assembly further comprises a seal disposed on said end face.

5. The system of claim 1, wherein said conical surface of said adapter body includes at least one circumferential sealing element.

6. The system of claim 1, wherein said second elasticity is greater than said first elasticity.

7. The system of claim 1, wherein:
said adapter body defines a longitudinal axis and has a first body segment extending along said longitudinal axis and defining said first conical surface;
said adapter body has a second body segment extending from said first body segment along said longitudinal axis;
said second body segment defines an outer surface interrupted to provide a change in cross section transverse to said longitudinal axis wherein said change in cross section is defined by at least one of the following:
a groove formed in said outer surface of said second body segment; and,
an annular collar extending radially outward from said outer surface of said second body segment;
to permit engagement of said adapter body by said stripper device to facilitate separation of said adapter body from said counterpiece.

8. An adapter assembly comprising:
a capillary having a forward end and a rearward end;
an adapter body having a passage in which said rearward end of said capillary is accommodated and said adapter body having a first conical surface facing away from said forward end of said capillary;
a counterpiece having a connector end and having a second conical surface opposite to said connector end, said second conical surface corresponding in conjugation to said first conical surface; said adapter body is received in or on said second conical surface causing said first and second conical surfaces to be in mutual contact engagement and conjointly define a conical interface forming an interference fit;
said first conical surface being defined by a first material having a first elasticity; and,
said second conical surface being defined by a second material having a second elasticity different from said first elasticity to provide a sealing at said conical interface.

9. The adapter assembly of claim 8, wherein:
said adapter body defines a longitudinal axis and has a first body segment extending along said longitudinal axis and defining said first conical surface;
said adapter body has a second body segment extending from said first body segment along said longitudinal axis;
said second body segment defines an outer surface interrupted to provide a change in cross section transverse to said longitudinal axis wherein said change in cross section is defined by at least one of the following:
a groove formed in said outer surface of said second body segment; and,
an annular collar extending radially outward from said outer surface of said second body segment;
to permit engagement and holding of said adapter body.

* * * * *